US 7,488,580 B1

(12) United States Patent
Naser

(10) Patent No.: US 7,488,580 B1
(45) Date of Patent: Feb. 10, 2009

(54) **PROTOCOL FOR DETECTION OF *MYCOBACTERIUM AVIUM* SUBSPECIES *PARATUBERCULOSIS* IN BLOOD**

(75) Inventor: Saleh A. Naser, Orlando, FL (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 0 days.

(21) Appl. No.: 11/370,648

(22) Filed: Mar. 8, 2006

Related U.S. Application Data

(60) Provisional application No. 60/660,417, filed on Mar. 10, 2005.

(51) Int. Cl.
*C12Q 1/68* (2006.01)
*C12P 19/34* (2006.01)

(52) U.S. Cl. .......................... 435/6; 435/91.2

(58) Field of Classification Search ........................ None
See application file for complete search history.

(56) References Cited

U.S. PATENT DOCUMENTS

2004/0260078 A1* 12/2004 Hermon-Taylor et al. .. 536/23.1

OTHER PUBLICATIONS

Bull et al. Detection and verification of *Mycobacterium avium* subsp. *paratuberculosis* in fresh ileocolonic mucosal biopsy specimens from individuals with and without Crohn's disease. J. Clin. Microbiol. (2003) 41:2915-2923.*
Gwozdz et al. Detection of *Mycobacterium avium* subsp. *paratuberculosis* in ovine tissues and blood by the polymerase chain reaction. Veterinary Microbiol. (1997) 51:233-244.*
Weiss et al. Differential responses of bovine macrophages to *Mycobacterium avium* subsp. *paratuberculosis* and *Mycobacterium avium* subsp. *avium*. Infection and Immunity (2002) 70:5556-5561.*
Naser, S.A., Ghobrial, G., Romero, C., Valentine, J.F., *Culture of Mycobacterium avium Subspecies paratuberculosis from the blood of patients with Crohn's Disease*, The Lancet (Sep. 18, 2004) vol. 364, pp. 1039-1044.
Naser, S.A., *Research Highlights, Crohn's Disease: New Evidence of Mycobacterial Involvement*, Nature Clinical Practice Gastroenterology & Hepatology, (Dec. 2004) vol. 1 No. 2 p. 68.
Naser, S.A. et al., Abstract presented at the 104th General Meeting of the American Society of Microbiology (ASM) on May 23-27, 2004, New Orleans, LA, *Detection of Mycobacterium avium subsp. paratuberculosis DNA in Blood from Crohn's Disease Patients*.
Ghobrial, G. et al., *Detection of Mycobacterium avium subsp. paratuberculosis DNA in Blood from Crohn's Disease Pateients*,
Program Issue, Florida Scientist, 68th Annual Meeting, University of Central Florida, Orlando Florida, Mar. 11-13, 2004, vol. 67 Supplement 1, ISSN: 0098-4590, 10:00a.m.MED-8.
Naser, SA Schwartz, D. Shafran, I., "Isolation of *Mycobacerium avium* subsp *paratuberculosis* from breast milk of Crohn's disease patients" *Am JL Gastroenterol* 2000, 95:1094-5.
Mishina, D Katsel, P Brown, St Gilberts, EC Greenstein RJ "On the Etiology of Crohn Disease" *Proc Natl Acad Sci USA* 1996, 93: 9816-20.
Schwartz, D, Schafran, I, Romero, C, et al. "Use of short-term culture for identification of *Mycobacterium avium* subsp *paratuberculosis* in tissue from Crohn's disease patients." *Clin Microbiol Infect* 2000, 6: 303-07.
Forbes.com "Study Supports Bacterial Cause for Crohn's" [online] Forbes.com, Lifestyle, Health, 3 pages, [retrieved on Feb. 17, 2005] Retrieved from: http://www.forbes.com/lifestyle/health/feeds/hscout/2004/09/16/hscout5212.66.html.
News in Science- "*Sheep Bug Linked to Crohn's Disease*"-Sep. 17, 2004 [online] ABC Online Home, science, news, stories, 2 pages, [retrieved on Feb. 17, 2005] Retrieved from: http://www.abc.net.au//science/news/stories/s12014505.html.
MSNBC-*Animal bacteria linked to Crohn's disease*, [online] MSNBC home, health, 3 pages, [retrieved on Feb. 17, 2005] Retrieved from: http://msnbc.msn.com/id/6020970/.
BBC News *Clear bacteria link to Crohn's*, [online] bbc.co.uk, BBC News, Health, Medical Notes, 3 pages, [retrieved on Feb. 17, 2005] Retrieved from: http://news.bbc.co.uk/1/hi/health/3663336.stm.
*Bug May Cause Crohn's Disease*, [online] WebMD Today, WebMDHealth, 3 pages, [retrieved on Feb. 17, 2005] Retrieved from: http://my.webmd.com/content/article/94/102697.htm?src=rss_cbsnews.
*A New Study on MAP Shows Progress, but Further Study Still Required*, [online] Crohn's & Colitis Foundation of America, 2 pages, [retrieved on Jan. 17, 2005] Retrieved from: http://www.ccfa.org/about/news/MAP.
*Crohn's disease Is a particular type of bacteria to blame?*, [online] USNew.com: Health: In Brief: Digestive Health: Crohn's disease (Dec. 16, 2004), 2 pages [retrieved on Jan. 17, 2005] Retrieved from: http://www.usnews.com/usnews/health/briefs/digestivehealth/hb041216a,htm.

* cited by examiner

*Primary Examiner*—Kenneth R. Horlick
*Assistant Examiner*—David C Thomas
(74) *Attorney, Agent, or Firm*—Brian S. Steinberger; Frances Olmsted; Law Offices of Brian S. Steinberger, P.A.

(57) ABSTRACT

A method and kit for detection of *Mycobacterium Avium* Subspecies Paratuberculosis (MAP) in blood and blood derivative samples from humans by culture and PCR. Technology can screen for MAP in blood samples from millions of patients having inflammatory and non-inflammatory bowel diseases, and the results are used to identify those patients with MAP for treatment by antibiotics. The method and kit can monitor and evaluate the outcome of therapy.

18 Claims, 7 Drawing Sheets

Sequence ID 1 P90 5-GTTCGGGGCCGTCGCTTAGG-3

Figure 1

Sequence ID 2 P91 5-GAGGTCGATCGCCCACGTGA-3

Figure 2

Sequence ID 3 AV1 5-ATGTGGTTGCTGTGTTGGATGG-3

Figure 3

Sequence ID 4 AV2 5-CCGCCGCAATCAACTCCAG-3

Figure 4

PROTOCOL FOR DETECTION OF *MYCOBACTERIUM AVIUM* SUBSPECIES *PARATUBERCULOSIS* IN BLOOD

This invention claims the benefit of priority from U.S. Provisional Patent Application Ser. No. 60/660,417 filed Mar. 10, 2005.

FIELD OF THE INVENTION

This invention relates to the detection of the bacterium *Mycobacterium Avium* Subspecies Paratuberculosis (MAP), and in particular to a method and kit for using blood via PCR and culture to detect patients having the bacterium and ultimately to select those patients having the bacterium for treatments.

BACKGROUND AND PRIOR ART

Inflammatory bowel diseases, such as Crohn's disease or ulcerative colitis cause inflammation of the gastrointestinal tract, most commonly the small intestine, with resulting abdominal pain, difficulty in digesting food, and other symptoms. Clinically diagnosing Crohn's or ulcerative colitis is an expensive, time consuming process which often requires some form of anesthesia. Generally, such diagnosis is made by performing an endoscopy, colonoscopy, sigmoidoscopy or radiological technique which often must be done in a hospital or clinic-like setting and sometimes requiring a biopsy of apparently affected tissue. It is estimated that at least one million Americans have Inflammatory Bowel Disease (IBD), with about 50% having Crohn's disease and about 50% having ulcerative colitis. Because of health care costs and diagnostics, the actual estimated number of patients with IBD may be significantly higher. Therefore it would be highly desirable to have a diagnostic test that is less invasive, less expensive and can accurately identify those patients with MAP infection. Ultimately, treatment with appropriate antibiotics will go a long way toward relieving them from the disease.

Based on the clinical similarities of animals infected with paratuberculosis, early research suggested that the disease which came to be known as Crohn's disease was caused by mycobacteria Early studies on Crohn's disease did not detect MAP in tissues from patients with Crohn's disease by conventional staining and culture techniques because such patients may have mycobacterium which are cell-wall deficient, and because of the difficulties in cultivating MAP, with its slow growing characteristics. A research group at Baylor College of Medicine patented the discovery of p36 (a protein from MAP) for serologic detection of MAP antibodies from Crohn's patients in U.S. Pat. No. 5,776,699. Researchers have also recently utilized the insertion element IS 900 to accurately identify MAP (Mishina, D Katsel, P Brown, S t Gilberts, E C Greenstein R J "On the Etiology of Crohn Disease" *Proc Natl Acad Sci USA* 1996, 93: 9816-20.) and others have found MAP in tissue and breast milk samples from lactating mothers with Crohn's disease (D. Schwartz et al., "Use of short-term culture for identification of *Mycobacterium avium* subsp paratuberculosis in tissue from Crohn's disease patients" *Clin Microbiol Infect* 2000: 6, 303-307. Naser, S A Schwartz, D. Shafran, I, "Isolation of *Mycobacterium avium* subsp paratuberculoisis from breast milk of Crohn's disease patients" *Am Jl Gastroenterol* 2000, 95:1094-5.

At the present time, however, no one has provided a method for diagnosing Crohn's disease that is caused by MAP (there may be other etiologies for Crohns or irritable bowel syndrome other than MAP) using a simple blood test. This blood test can also be used to identify Crohn's disease patient population with MAP infection. Additonally, this novel blood test can be used to differentiate IBD patients with MAP infection from those without MAP infection. Moreover, such tests can be used to monitor and evaluate treatment after obtaining a first positive result. Repeat blood tests can determine if the bacterium is being reduced or eliminated from the system, or not.

SUMMARY OF THE INVENTION

A primary objective of the present invention is to provide for using blood via PCR and culture to detect MAP.

A second objective of the invention is to provide a method to diagnose those patients with Crohn's disease or ulcerative colitis caused by the bacterium.

A third objective of the invention is to ultimately select those persons who would benefit by anti-MAP treatment.

A method is provided for monitoring and evaluating the course of irritable bowel disease by determining the presence or absence of irritable bowel disease caused by MAP after the initial diagnosis, and through treatment.

A preferred method of diagnosing inflammatory bowel disease in those patients who have bowel disease caused by *Mycobacterium Avium* Paratuberculosis (MAP) using a sample of peripheral blood tissue includes selecting a blood sample from at least a single patient of selected patients, culturing that blood sample for a period of time sufficient to obtain a sufficient growth of MAP to subject to PCR, and detecting MAP therefrom.

The preferred method is used when the patient is a human patient having inflammatory bowel disease which is known as Crohn's disease, irritable bowel disease (IBD), or Ulcerative colitis. A more preferred method further includes treating MAP infected patients who have MAP detected in their blood with an anti-MAP effective amount of an anti-MAP compound and a pharmaceutically acceptable excipient therefor.

A preferred method of treating MAP infected patients includes using an anti-MAP compound that is an antibiotic in an effective amount is an amount sufficient to eliminate MAP from registering positive in a blood test.

The preferred method of treating MAP infected patients includes a time required to culture the blood sample of from approximately 8 weeks to approximately 12 weeks, preferably 12 weeks. The blood sample is cultured in media selective for MAP that includes Mycobacterial Growth Indicator Tube (MGIT), BACTEC or BACTEC further supplemented with 1% sucrose.

The preferred method of treating MAP infected patients further includes the use of the PCR method to detect MAP using one of more of the group consisting of Seq ID 1, Seq ID2, Seq ID 3 and Seq ID 4 as primers for nested PCR or the method can include the use of. primers that include one or more of the group consisting of Seq ID 1, Seq ID 2, Seq ID 3 and Seq ID 4 and nucleotide polymorphisms thereof.

It is also within the present invention to use one or more of Seq ID 1 or Seq ID 2 as primers in the first round of PCR and one or more of Seq ID 3 or Seq ID 4 in the second round of PCR.

The present invention also includes a preferred method for monitoring and evaluating the course of inflammatory bowel disease caused by MAP that includes selecting a blood sample from at least a single patient of selected patients, culturing that blood sample for a period of time sufficient to obtain a sufficient growth of MAP to subject to PCR, detecting MAP therefrom, obtaining a positive result for MAP, and continuing to repeat said test at intervals throughout treatment.

The method for treatment of the inflammatory bowel disease known as Crohn's disease requires a volume of blood extracted from the patient for use in the test in an amount of approximately 4 mls or greater.

A preferred kit for use in diagnosing inflammatory bowel disease caused by *Mycobacterium Avium* Paratuberculosis (MAP) in blood includes primers, Seq ID1, Seq ID2, Seq ID3 and Seq ID4.

Further objects and advantages of this invention will be apparent from the following detailed description of the presently preferred embodiments which are illustrated schematically in the accompanying drawings.

BRIEF DESCRIPTION OF THE FIGURES

FIG. 1 is Seq ID 1-P90 primer
FIG. 2 is Seq ID 2-P91 Primer
FIG. 3 is Seq ID 3-AV1 Primer
FIG. 4 is Seq ID 4-AV2 Primer

DESCRIPTION OF THE PREFERRED EMBODIMENTS

Before explaining the disclosed embodiments of the present invention in detail it is to be understood that the invention is not limited in its applications to the details of the particular arrangements shown since the invention is capable of other embodiments. Also, the terminology used herein is for the purpose of description and not of limitation.

Blood samples were taken from patients, and drawn into sterile K2-EDTA vacutainer tubes. A sample of each buffy coat (the middle layer of blood products) were used to inoculate into media that is selective for Mycobacterium avian subsp paratuberculosis (MAP). Such media may be Mycobacterial Growth Indicator Tubes (MGIT) or MGITpara (purchased from Becton Dickinson, Franklin Lake, N.J.) or BACTEC (purchased from Beckton Dickinson, Franklin Lake, N.J.) or other selective media and added to 4 ml of modified Middlebrook 7H9 broth base. The media is optimally supplemented with 0.1% sucrose, Mycobactin J (Allied Monitor) and PANTA (Becton Dickinson, Franklin Lake, N.J.) as described in Schwartz, D, Schafran, I, Romero, C, et al. "Use of short-term culture for identification of *Mycobacterium avium* subsp paratuberculosis in tissue from Crohn's disease patients." *Clin Microbiol Infect* 2000, 6: 303-307. MAP requires long term culturing, and the cultures were incubated for 8-12 weeks.

Figure 5:
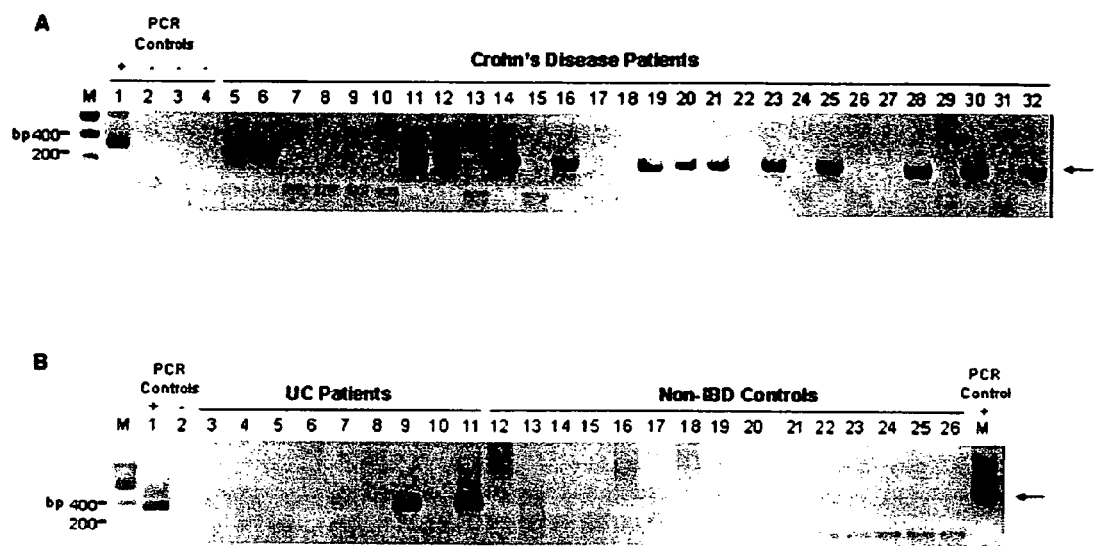
FIG. 5 is an autoradiograph of Nested PCR detection of MAP DNA from cultured peripheral blood samples

Cultures were assessed for the presence of MAP by staining and then subjecting to nested PCR. Genomic DNA was extracted and oligonucleotide primers were derived from the DNA insertion sequence IS900, which is unique to MAP. The primers P90 (Sequence ID 1 in FIG. 1) and P91 (Sequence ID 2 in FIG. 2) were used for the first round to amplify a unique 398 bp fragment of the IS900 gene. The sensitivity and specificity for the amplified MAP DNA fragment were achieved by use of AV1 (Sequence ID 3 in FIG. 3) and AV2 (Sequence ID 4 in FIG. 4) oligonucleotide primers in the second round to re-amplify an 298 base pair internal nucleotide sequence for the 398 base pair template as shown in FIG. 5. In FIG. 5, positive results are indicated by a bright 298 bp band (arrow) on 2% agarose gel electrophoresis. M=molecular weight marker. Lane 1 represents DNA from MAP strain ATTC 43015 as a positive control (+); lanes A2 and B2 represent negative controls for second round of nested PCR, lanes A3 and A4 represent negative controls for first round of nested PCR and for DNA extraction steps, respectively. Positive and negative controls were run along with each sample analysis. For the composite image shown in FIG. 5, only representative positive and negative controls are shown. FIG. 5 results are shown for Crohn's Disease Patients, Ulcerative colitis (UC) Patients and Patients with No Inflammatory Bowel Disease (Non-IBD).

The PCR conditions consisted of a reaction medium of 5-mM MgCl2, 0.2 mM dNTP, 6% DMSO or 0.5M Betaine, 2 micromolar primers and 2.5 units of Platinum Taq polymerase purchased from Invitrogen, Calsbad Calif. or 1 unit of TFL DNA polymerase purchased from Promega, Madison, Wi. and 10 microliters of DNA template. The PCR reaction mixture in the second round of the nested PCR was the same, except that 5 microliters of PCR product from the first round was used as a template and the AV1 and AV2 oligonucleotide primers were substituted. The PCR cycling conditions were 95 degrees C. for 5 min, 34 cycles of 95 degrees for 1 minute and 58 degrees C. for 1.5 minutes, 72 degrees C. for 1.5 minutes and a final extension of 10 minutes at 72 degrees C. The amplification product size was assessed on 2% agarose gel, however one can also use real time PCR using the above condition where agarose gel may not be needed for reading the results. The same protocol may be applied using quantitative real time PCR.

Once positive tests are obtained using this method, patients can be treated using anti-MAP compounds. Such compounds may be antibiotics. Antibiotics with known specificities for MAP are Clarithromycin, Rifabutin and Clofazimine.

Example 1

Patients and Samples: 52 participants were included in the study: 28 with Crohn's disease, nine with ulcerative colitis and 15 without inflammatory bowel disease (two with colon cancer, one with diverticulitis, one with gastrooesophageal reflux and 11 healthy individuals). Informed consent was obtained in accordance with institutional review board regulations at the University of Florida, Gainesville Veterans Affairs Medical Center, and the University of Central Florida. Of the patients with Crohn's disease, 22 of 28 (78%) and all the patients with ulcerative colitis were recruited from the inflammatory bowel disease clinic at the University of Florida, a tertiary referral centre. The diagnosis of Crohn's disease or ulcerative colitis was established on standard clinical, endoscopic, histological, and radiographic criteria. Disease activity was assessed by use of the Harvey Bradshaw index or the clinical findings of the treating physician. Only one of the patients with Crohn's disease, and none of those with ulcerative colitis, were newly diagnosed. Patients with indeterminate colitis were excluded. Two 4-mL whole blood samples drawn into sterile K2-EDTA Vacutainer tubes were obtained from every participant. All samples were coded to conceal the patient's identity and the diagnosis. The samples were immediately processed in a class II biosafety cabinet. The buffy coat layer from each tube was transferred into a separate sterile tube that was used for either genomic DNA extraction or culture. A medication history was completed for each participant as shown in Table 1. Use of prednisone, budesonide, azathioprine, mercaptopurine, methotrexate, or infliximab at any dose was judged to be immunosuppressive. Products containing mesalamine were not considered to be immunosuppressive. Procedures for culture, each buffy coat sample was resuspended in 1 mL of sterile phosphate buffer saline, pH 6.8. Samples (0.5 mL) of the suspension were used to inoculate one MGIT and one 12B* BACTEC bottle (Beckton Dickinson, Franklin Lake, N.J., USA), each containing 4 mL of modified Middlebrook 7H9 broth base media (Becton Dickinson) with supplements as previously described. All inoculated culture media were incubated at 37° C. in a 5% carbon dioxide incubator. The BACTEC bottles were assessed every week with the BACTEC 460TB Analyzer (Becton Dickinson) and the MGIT were checked every 2 weeks for visible turbidity and fluorescence-quenching activity with a 365 nm UV-illuminator. The BACTEC bottles with a growth index reading of 50 or more, and all MGIT cultures incubated for 8-12 weeks, were assessed for the presence of MAP by staining and nested PCR. MAP cells were inactivated by heating the cell pellet from a 0-5 mL sample of the culture in 500 µL TE buffer (10 mM Tris and 1 mM EDTA, pH 8.0 HCl) at 80° C. for 10 min. The sample was centrifuged at 10000 rpm (12800 g) for 5 min and the cell pellet was suspended in 150 µL of sterile water. 50 µL was used to prepare smears for Ziehl-Neelsen staining, acridine orange staining, or immunostaining with adsorbed rabbit-anti-MAP polyclonal IgG antibodies as described previously. The remaining volume was used for extraction of genomic DNA for PCR analysis.

Analysis of DNA: Genomic DNA was extracted from uncultured buffy coat cells and cell culture pellets in a separate class II biosafety cabinet. The cells were re-suspended in 100 µL sterile TE buffer and incubated in a dry heat bath at 100° C. for 30 min, then placed on ice for 15 min. They were then centrifuged at 12000 rpm (18500 g) and 4° C. for 10 min. The supernatant was transferred to 2.0 mL phase-lock gel tubes (PLG, Eppendorf, Westbury, N.Y., USA). 200 µl of phenol/chloroform/isoamyl alcohol (1:1:24 v/v; Acros Organics Morris Plains, N.J., USA) was added, mixed, and centrifuged at 12000 rpm (18500 g) and 4° C. for 5 min. The nucleic acid was precipitated, washed, dried, and dissolved in 50 µL of sterile water. Both primary and secondary rounds of the nested PCR were done in a class II biosafety cabinet used only for PCR. Oligonucleotide primers were derived from the DNA insertion sequence IS900, which is unique to MAP. The primers P90 and P91 (Sequence ID 1 in FIG. 1 and Sequence ID 2 in FIG. 2, respectively) were used for the first round to amplify a unique 398 bp fragment of the IS900 gene. The sensitivity and specificity for the amplified MAP DNA fragment were achieved by use of AV1 and AV2 oligonucleotide primers (Sequence ID 3 in FIG. 3 and Sequence ID 4 in FIG. 4, respectively) in the second round to re-amplify an 298 bp internal nucleotide sequence of the 398 bp template. The PCR reaction mixture consisted of 40 µL PCR buffer: 5-mM MgCl2, 0.2 mM dNTP, 6% DMSO or 0.5 M Betaine, 2 µM primers, and 2.5 U Platinum Taq polymerase (Invitrogen, Carlsbad, Calif., USA) or 1 U TFL DNA polymerase (Promega, Madison, Wis., USA) and 10 µl of DNA template. The PCR reaction mixture in the second round of the nested PCR was the same, except that 5 µL of PCR product from the first round was used as a template and the AV1 and AV2 oligonucleotide primers were substituted. The PCR cycling conditions were: 95° C. for 5 min, 34 cycles of 95° C. for 1 min, 58° C. for 1.5 min, 72° C. for 15 min, and a final extension of 10 min at 72° C. The amplification product size was assessed on 2% agarose gel. Negative controls for PCR consisted of sterile TE buffer or sterile water used in place of the DNA template, and were used in parallel with every round of PCR preparation. Positive MAP DNA from strain ATCC 43015 was prepared independently and added to PCR tubes at a different facility using separate supplies. Nucleotide sequencing verified the specificity of the amplified IS900 fragment. PCR products from the second round of the nested PCR from positive samples were purified and sequenced at the Biomolecular Science Center DNA Sequencing Core facility at the University of Central Florida. BLAST and alignment sequence analyses were also done.

Figure 6A:
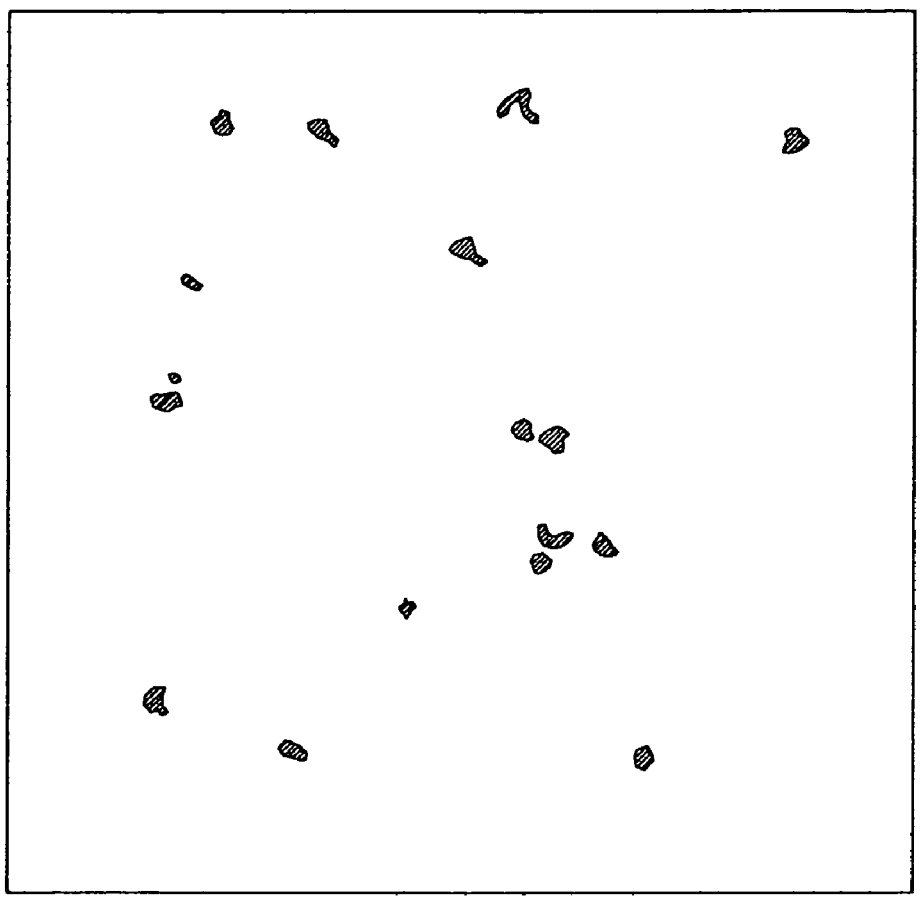
FIG. 6A is a drawing of microscopic MAP cultures isolated from blood (5 week old MGIT culture from patient with Crohn's disease)
Figure 6B:
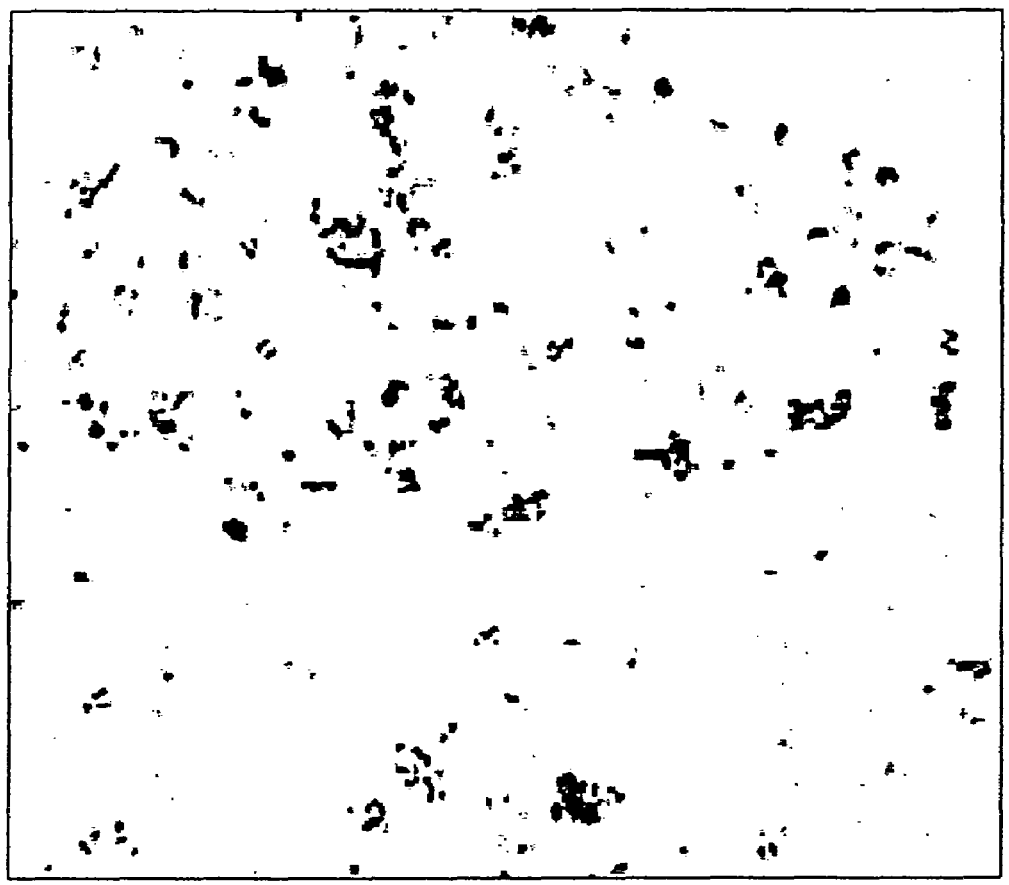
FIG. 6B is a representative acid-fast positive MAP culture from a patient with Crohn's disease after 12 weeks of incubation.

Statistical Analysis: Groups were compared with 2×2 contingency tables and Fishers exact test. A positive (p) value of less than 0.05 was judged to be significant. Results: The code for concealment of participants' identities and diagnoses was broken and data were tabulated after the conclusion of all experiments (table 1). Participants were aged 18-77 years. Overall, 50% were female; 17 (61%) of those with Crohn's disease, 2 (22%) of those with ulcerative colitis, and 7 (47%) of those without inflammatory bowel disease. 16 (62%) of the 26 patients with Crohn's disease for whom data were available were known to be on immunosuppressive medications. Four (44%) patients with ulcerative colitis and none of those without inflammatory bowel disease were on such medications. Samples that were positive for the MAP-specific IS900 element clearly showed a single bright 298 bp band on 2% agarose gel. MAP DNA was detected in 20 of 52 (38%) of all blood samples (table); 13 (46%) patients with Crohn's disease, four (44%) with ulcerative colitis, and three (20%) without inflammatory bowel disease. None of the PCR internal controls, including one for genomic DNA extraction and one in each round of the nested PCR, were positive for MAP DNA, indicating no laboratory contamination. Nucleotide sequencing of purified MAP DNA fragments from representative samples that were positive in the second round of the nested PCR confirmed the amplification of IS900 nucleotide sequence. After 12 weeks of incubation, possible mycobacterial growth was detected in three of 52 BACTEC cultures. Detection of possible mycobacterial growth in MGIT cultures inoculated with blood-derived buffy coat based on the observation of visible turbidity and increase in fluorescence intensity is unreliable. AB 52 MGIT cultures and the three BACTEC cultures in which a possible mycobacterial growth was detected were assessed for the presence of MAP. IS900-nested PCR identified MAP in all three suspected BACTEC cultures and in 14 of 52 MGIT cultures. Only one patient was positive for MAP by both culture methods. MAP was isolated from culture in 14 (50%) patients with Crohn's disease, two (22%) of those with ulcerative colitis, and none of those without inflammatory bowel disease (p=0.0005 for group with Crohn's disease vs without inflammatory bowel disease; see FIG. 5). 11 of the 13 patients with Crohn's disease who were positive for MAP DNA in blood by PCR were also positive by culture, and ten of the 14 subsequently found to be positive by culture had also tested positive by PCR. Of the four PCR-positive patients with ulcerative colitis, one was positive by culture; the other culture-positive ulcerative colitis patient was PCR negative. None of the three PCR-positive individuals without inflammatory bowel disease was positive by culture. Among the 26 Crohn's disease patients for whom data on the use of immunosuppressive medications were available, current use of immunosuppressive medication did not correlate with a positive culture result (p=0.23; table). The sample size was too small to make any distinction about specific immunosuppressive medications, age of onset, disease duration, or clinical phenotype. MAP-positive cultures of buffy coat were negative by acid-fast Ziehl-Neelsen staining during the early weeks of culture incubation, but were positive by acridine orange or immunostaining with rabbit anti-MAP IgG polyclonal antibodies as shown in FIG. 6A. FIG. 6A is an illustration of a cell-wall-deficient MAP from 5-week-old MGIT culture from patient with Crohn's disease. After 12 weeks of incubation, all 16 MAP-positive cultures contained acid fast bacilli, with the occasional presence of deformed cells containing remnant cell wall components, also known as pre-spheroplasts as shown in FIG. 6B. FIG. 6B is a representative acid-fast positive MAP culture from a patient with Crohn's disease.

tutions (CG instead of GC located at 114-115 of the 1451 bp encoding sequence of the IS900 locus) in seven MAP clinical isolates. Only one IS900 locus (accession number X16293) showed no CG switching.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

```
                          SEQUENCE LISTING

<160> NUMBER OF SEQ ID NOS: 4

<210> SEQ ID NO 1
<211> LENGTH: 20
<212> TYPE: DNA
<213> ORGANISM: mycobacterium Avium

<400> SEQUENCE: 1
gttcggggcc gtcgcttagg                                                20

<210> SEQ ID NO 2
<211> LENGTH: 20
<212> TYPE: DNA
<213> ORGANISM: mycobacterium Avium

<400> SEQUENCE: 2
gaggtcgatc gcccacgtga                                                20

<210> SEQ ID NO 3
<211> LENGTH: 22
<212> TYPE: DNA
<213> ORGANISM: mycobacterium Avium

<400> SEQUENCE: 3
atgtggttgc tgtgttggat gg                                             22

<210> SEQ ID NO 4
<211> LENGTH: 19
<212> TYPE: DNA
<213> ORGANISM: mycobacterium Avium

<400> SEQUENCE: 4
ccgccgcaat caactccag                                                 19
```

To investigate the diversity of the MAP isolates, the 298 bp was sequenced and amplifed IS900 fragment from 11 representative MAP-positive cultures. The nucleotidesequences were assessed against each other, the sequence from the laboratory MAP strain (positive control), and several IS900 loci available in the National Center for Biotechnology Information database (http://www.ncbi.nlm.nih.gov). All sequences were confirmed as IS900. Nine of the 11 MAP isolates were different from each other because of nucleotide polymorphisms including insertions, deletions, and substitutions. All 11 MAP isolates differed from the MAP-positive control used in our laboratory. Of 11 IS900 loci published in the database, ten (accession numbers AF416985, AJ250023, AJ250022, AJ250015, AJ250016, AJ250017, AJ250018, AJ250019, AJ250020, AJ250021) showed two consecutive base substi-

I claim:

1. A method of diagnosing inflammatory bowel disease in those patients who have bowel disease caused by *Mycobacterium avium* subspecies paratuberculosis (MAP) using a sample of peripheral blood tissue comprising the steps of:

selecting a blood sample from at least a single patient of selected patients;

culturing the blood sample for a period of time sufficient to obtain a sufficient growth of MAP to subject to PCR; and detecting MAP therefrom, said PCR method used to detect MAP comprising using one or more of the group consisting of SEQ ID NO:1, SEQ ID NO:2, SEQ ID NO:3 and SEQ ID NO:4 as primers for nested PCR, said patients being human patients, and said sample of blood consisting of the buffy coat.

2. The method of claim 1, wherein the human patient has inflammatory bowel disease selected from at least one of: Crohn's disease, irritable bowel disease (IBD), and ulcerative colitis.

3. The method of claim 1 wherein the inflammatory bowel disease is Crohn's disease.

4. The method of claim 1, further comprising treating MAP infected patients who have MAP detected in their blood with an anti-MAP effective amount of an anti-MAP compound and a pharmaceutically acceptable excipient therefor.

5. The method of claim 2, further comprising treating MAP infected patients who have MAP detected in their blood with an anti-MAP effective amount of an anti-MAP compound and a pharmaceutically acceptable excipient therefor.

6. The method of claim 4 wherein said anti-MAP compound comprises an antibiotic.

7. The method of claim 6, wherein said effective amount is an amount sufficient to eliminate MAP from registering positive in a blood test.

8. The method of claim 1 wherein the time required to culture the blood sample is approximately 8 weeks to approximately 12 weeks.

9. The method of claim 8, wherein the time required to culture the blood sample is approximately 12 weeks.

10. The method of claim 1 where the blood sample is cultured in media selective for MAP.

11. The method of claim 1 wherein the media selective for MAP is selected from the group consisting of Mycobacterial Growth Indicator Tube (MGIT) or BACTEC.

12. The method of claim 11, wherein the MGIT or BACTEC is further supplemented with 1% sucrose.

13. The method of claim 1 wherein the primers comprise one or more of the group consisting of Seq ID 1, Seq ID 2, Seq ID 3 and Seq ID 4 and nucleotide polymorphisms thereof.

14. The method of claim 1 wherein one or more of Seq ID 1 or Seq ID 2 are used as primers in the first round of PCR and one or more of Seq ID 3 or Seq ID 4 were used in the second round of PCR.

15. The method, as in claim 13 wherein one or more of Seq ID 1 or Seq ID 2 are used as primers in the first round of PCR and one or more of Seq ID 3 or Seq ID 4 are used in the second round of PCR.

16. A method for monitoring and evaluating the course of inflammatory bowel disease caused by MAP comprising:
    selecting a blood sample from at least a single patient of selected patients;
    culturing the blood sample for a period of time sufficient to obtain a sufficient growth of MAP to subject to PCR;
    detecting MAP therefrom;
    obtaining a positive result from MAP; and
    continuing to repeat said test at intervals throughout treatment wherein the method PCR method used to detect MAP comprises using one of more of the group consisting of SEQ ID NO:1, SEQ ID NO:2, SEQ ID NO:3 and SEQ ID NO:4 as primers for nested PCR, said patients being human patients, and said sample of blood consisting of the buffy coat.

17. The method, as in claim 16 wherein the inflammatory bowel disease is Crohn's disease.

18. The method, as in claim 1 wherein the volume of blood extracted from the patient for use in the test is 4 mls or greater.

* * * * *

UNITED STATES PATENT AND TRADEMARK OFFICE
CERTIFICATE OF CORRECTION

| | |
|---|---|
| PATENT NO. | : 7,488,580 B1 |
| APPLICATION NO. | : 11/370648 |
| DATED | : February 10, 2009 |
| INVENTOR(S) | : Saleh A. Naser |

It is certified that error appears in the above-identified patent and that said Letters Patent is hereby corrected as shown below:

Col. 1 lines 8-9 should read

STATEMENT REGARDING FEDERALLY SPONSORED RESEARCH OR DEVELOPMENT

This invention was funded in part by National Institutes of Health, contract number 5R01AI051251. The government has certain rights in this invention.

Signed and Sealed this
Tenth Day of May, 2011

David J. Kappos
*Director of the United States Patent and Trademark Office*